US009082518B2

(12) United States Patent
Hiratsuka et al.

(10) Patent No.: US 9,082,518 B2
(45) Date of Patent: Jul. 14, 2015

(54) NUCLEAR REACTOR VIBRATION MONITORING APPARATUS AND METHOD OF MONITORING NUCLEAR REACTOR VIBRATION

(71) Applicant: Hitachi-GE Nuclear Energy, Ltd., Hitachi-shi, Ibaraki (JP)

(72) Inventors: Masahiro Hiratsuka, Tokyo (JP); Atsushi Baba, Ibaraki (JP); Masahiro Koike, Hitachi (JP); Taro Ikezumi, Hitachinaka (JP); Minoru Ootaka, Takahagi (JP)

(73) Assignee: Hitachi-GE Nuclear Energy, Ltd., Hitachi-shi (JP)

( * ) Notice: Subject to any disclaimer, the term of this patent is extended or adjusted under 35 U.S.C. 154(b) by 157 days.

(21) Appl. No.: 13/672,189

(22) Filed: Nov. 8, 2012

(65) Prior Publication Data

US 2013/0121451 A1    May 16, 2013

(30) Foreign Application Priority Data

Nov. 11, 2011    (JP) .................................. 2011-247583
Nov. 28, 2011    (JP) .................................. 2011-258464

(51) Int. Cl.
*G21C 17/003*    (2006.01)
*G21C 15/25*    (2006.01)
(Continued)

(52) U.S. Cl.
CPC .............. *G21C 17/003* (2013.01); *G01N 29/07* (2013.01); *G01N 29/46* (2013.01); *G21C 15/25* (2013.01); *G21C 17/10* (2013.01); *G01N 2291/044* (2013.01); *Y02E 30/31* (2013.01)

(58) Field of Classification Search
CPC ....... G21C 17/003; G21C 17/10; G21C 15/25
USPC ..................... 376/245, 249, 258, 259; 73/590
See application file for complete search history.

(56) References Cited

U.S. PATENT DOCUMENTS 3,753,852 A * 8/1973 Scott et al. ..................... 376/249
7,344,493 B2   3/2008 Sonnenschein et al.
(Continued)

FOREIGN PATENT DOCUMENTS

GB         1294210      * 10/1972
JP      58-223008 A     12/1983
(Continued)

OTHER PUBLICATIONS

Atsuta Yoshimichi et al., "High Accuracy Continuous Monitoring of Wall Thinning in High Temperature Environment", IIC Review, No. 42, 2009, (three (3) pages).
The Japan Society of Mechanical Engineers, JSME, Steam Table, Based on IAPWS-IF97, 1999, pp. 128-129.

*Primary Examiner* — Jack W Keith
*Assistant Examiner* — Daniel Wasil
(74) *Attorney, Agent, or Firm* — Crowell & Moring LLP

(57) ABSTRACT

Vibration of a jet pump installed in a reactor pressure vessel of a boiling water reactor is monitored. Ultrasonic waves are transmitted from an ultrasonic sensor installed on an outer surface of the reactor pressure vessel toward a throat and a diffuser of the jet pump. When the ultrasonic waves reach respective outer surfaces of the throat and diffuser, reflected waves are generated at the respective outer surfaces. The ultrasonic sensor receives those reflected waves. The ultrasonic signal process section obtains a distance in the horizontal direction between the throat and the diffuser based on a time difference of the reflected waves reflected from respective reflection surfaces of the throat and diffuser and a sound speed in reactor water in the neighborhood of the throat and diffuser. A relative vibration is obtained based on the change with time of the distance.

14 Claims, 14 Drawing Sheets

(51) Int. Cl.
  *G21C 17/10* (2006.01)
  *G01N 29/07* (2006.01)
  *G01N 29/46* (2006.01)

(56) References Cited

U.S. PATENT DOCUMENTS

| | | | |
|---|---|---|---|
| 7,578,191 B2 * | 8/2009 | Kasik et al. | 73/590 |
| 8,701,493 B2 * | 4/2014 | Watanabe et al. | 376/249 |
| 8,774,340 B2 * | 7/2014 | Sato et al. | 376/249 |
| 2010/0202581 A1 * | 8/2010 | Kitajima et al. | 376/245 |
| 2011/0154900 A1 | 6/2011 | Watanabe et al. | |
| 2012/0285246 A1 * | 11/2012 | Kuroda et al. | 73/590 |

FOREIGN PATENT DOCUMENTS

| | | |
|---|---|---|
| JP | 61-31130 A | 2/1986 |
| JP | 6-4789 A | 1/1994 |
| JP | 11-125688 A | 5/1999 |
| JP | 2004-528074 A | 9/2004 |
| JP | 3782559 B2 | 6/2006 |
| JP | 2009-68987 A | 4/2009 |
| JP | 2010-185884 A | 8/2010 |
| JP | 4551920 B2 | 9/2010 |
| JP | 2011-133241 A | 7/2011 |
| WO | WO 02/068988 A1 | 9/2002 |
| WO | WO 2011/077713 A1 | 6/2011 |

* cited by examiner

NUCLEAR REACTOR VIBRATION MONITORING APPARATUS AND METHOD OF MONITORING NUCLEAR REACTOR VIBRATION

CLAIM OF PRIORITY

The present application claims priority from Japanese Patent application serial no. 2011-247583, filed on Nov. 11, 2011 and Japanese Patent application serial no. 2011-258464, filed on Nov. 28, 2011, the content of which is hereby incorporated by reference into this application.

BACKGROUND OF THE INVENTION

1. Technical Field

The present invention relates to nuclear a reactor vibration monitoring apparatus and a method of monitoring nuclear reactor vibration, which monitor vibrational state of reactor internal including the jet pump installed in a reactor pressure vessel of a nuclear reactor.

2. Background Art

By referring to the case of a general boiling water reactor (BWR) as an example, an internal structure of a reactor pressure vessel (hereinafter, referred to as a RPV) and the jet pump will be explained. The boiling water reactor (BWR) has a RPV, as described in Japanese Patent No. 3782559. The RPV generally has an almost cylindrical shape, and one end thereof is closed by a bottom head, and the other end thereof is closed by a removable upper head. The jet pump is installed inside the RPV.

Due to the installation of the jet pump, cooling water more in volume than the amount of cooling water sucked outside the RPV can be supplied to a core by a recirculation pump.

The jet pump has a nozzle, a throat, and a diffuser. The throat and diffuser are connected to each other by a slip joint. A gap is formed between the throat and the diffuser. The nozzle is disposed above the throat. Driving water which is cooling water is jetted from the nozzle inward the throat. When there exists a pressure difference between outside and inside the slip joint, a part of cooling water flowing from the throat into the diffuser flows out from the jet jump through the gap.

As mentioned above, the jet pump generates an internal high-speed flow, a mixed flow, and a leakage flow from the gap of the slip joint, so that it is an apparatus affected by a flow-induced vibration. The vibrational state of the jet pump must be monitored and evaluated to ensure long-period soundness of the jet pump. The jet pump is an example of an apparatuses to be evaluated like this.

The method of monitoring vibration and vibration monitoring apparatus are, for example, described in Japanese Patent No. 3782559, and Japanese Patent No. 4551920. For example, Japanese Patent No. 3782559 describes the nuclear reactor vibration monitoring apparatus. In the nuclear reactor vibration monitoring apparatus, ultrasonic waves are transmitted from an ultrasonic sensor installed on an outside surface of the RPV to the jet pump via the RPV and reactor water in the RPV and the change of propagation time of the ultrasonic waves is measured based on ultrasonic velocity of the RPV, ultrasonic velocity of the reactor water, thickness of the RPV, and a distance between the RPV and a reactor internal in the RPV, thus the vibration amplitude of the reactor internal is obtained.

Further, in a vibration and degradation monitoring apparatus described in Japanese Patent No. 4551920, a corner reflector including a plane-shaped reflection surface capable of reflecting ultrasonic waves and an orthogonal plane as a reflection surface is attached to the surface of a monitoring object. The apparatus receives the ultrasonic waves reflected on the reflection surface of the reflection body and measures a vibration displacement of the monitoring object based on the received ultrasonic waves.

Furthermore, Japanese Patent Laid-Open No. 2011-133241 discloses a nuclear reactor vibration monitoring apparatus which can detect vibration of a reactor internal which is sloped and curved without attaching a reflection plate, by identifying and removing reflected ultrasonic pulses reflected from a wall inside of the RPV.

CITATION LIST

Patent Literature

[Patent Literature 1] Japanese Patent No. 3782559
[Patent Literature 2] Japanese Patent No. 4551920
[Patent Literature 3] Japanese Patent Laid-Open No. 2011-133241

Non Patent Literature

[Non Patent Literature 1] IIC REVIEW (2009/10), No. 42, pp. 39
[Non Patent Literature 2] The Japan Society of Mechanical Engineers, JSME, Steam Table, BASED ON IAPWS-IF97 (1999), pp. 128-129

SUMMARY OF THE INVENTION

Technical Problem

Damage due to vibration is greatly affected by a collision or metallic wear due to relative vibration of reactor internals. However, generally, the relative vibration accompanying with contact with another apparatus is narrower in amplitude than vibration of a single reactor internal and the measurement thereof is more difficult than the vibration measurement of the single reactor internal.

The aforementioned prior art discloses the technology of detecting vibration of a single reactor internal. When calculating the relative vibration by measuring the vibration of each of a plurality of reactor internals by a plurality of sensors using the conventional technology and obtaining the differences, a reduction in the accuracy may be worried due to the ultrasonic path by each sensor, ultrasonic intensity, and characteristics of a delay member.

Here, when monitoring the vibrational state of the reactor internal including the jet pump in the boiling water reactor, with respect to low alloy steel, stainless steel, a Ni group alloy, and reactor water which are media for propagating ultrasonic waves, the sound speed varies with temperature (for example, refer to IIC REVIEW (2009/10), No. 42, pp. 39). The sound speed change of mild steel is about 4% within the range from the room temperature to 300° C. Further, particularly, the sound speed of reactor water of the boiling water reactor changes by about 37% from 1531 m/s to 970 m/s while the temperature rises from 40° C. at end of in-service inspection to 300° C. at the time of the rated operation (for example, refer to The Japan Society of Mechanical Engineers, JSME, Steam Table, BASED ON IAPWS-IF97 (1999), pp. 128-129).

Therefore, for example, when an ultrasonic sensor is installed on an outer surface of the RPV, the elapsed time while ultrasonic waves transmitted from the ultrasonic sensor installed on the outer surface of the RPV are reflected from the monitoring object and are received again by the ultrasonic sensor is greatly changed in correspondence with the change in the sound speed due to the temperature condition under the condition that a temperature change is caused during operation of the reactor or during the rated operation at about 300° C. Furthermore, when such a temperature change is caused, the reactor internal and the RPV expand thermally and the relative position relationship between the ultrasonic sensor and the monitoring object when the ultrasonic sensor is installed is shifted. Therefore, in the ultrasonic measurement under such a condition, the reception time position of the ultrasonic echoes from the monitoring object position of the monitoring object is changed, so that multiple reflected echoes in the RPV, noise echoes caused by the spread of ultrasonic waves, and shape echoes which become measurement noise can be hardly distinguished and the ultrasonic echoes from the monitoring object position must be identified.

Further, to know the reception time position of the ultrasonic echoes from the monitoring object position, in consideration of the sound speed change of the ultrasonic propagation medium due to the temperature change and the relative position shift due to the temperature change, a correction by the propagation distance of each medium and the sound speed at the temperature is necessary.

The temperatures of the ultrasonic sensor and RPV can be simply measured by a temperature measuring apparatus such as a thermocouple. However, to measure the temperature of reactor water flowing through the monitoring object position, the temperature measuring apparatus must be installed in the RPV.

Furthermore, to evaluate the amplitude of the vibration at the monitoring object position with high precision, the temperature of the reactor water must be measured and the conventional technology cannot evaluate it.

As mentioned above, in the technology of monitoring the vibrational state of the reactor internal including the jet pump in the boiling water reactor, the sound speed of ultrasonic waves of the metal and reactor water which are media of the ultrasonic propagation path is changed, so that a problem arises that it is difficult to identify the reflected echoes from the monitoring object.

A first object of the present invention is to provide a reactor vibration monitoring apparatus and a method of monitoring nuclear reactor vibration which can monitor a minute relative vibration between reactor internals in a reactor pressure vessel to evaluate soundness and abnormality of the apparatuses.

A second object of the present invention is to provide a method of monitoring nuclear reactor vibration capable of easily identifying reflected echoes from a monitoring object when monitoring the vibrational state of reactor internal in a reactor pressure vessel using ultrasonic waves.

Solution to Problem

A first feature of the present invention for attaining the above first object is to irradiate ultrasonic waves oscillated from an ultrasonic sensor to a plurality of reactor internals vibrating relatively, process reflected waves from the plurality of reactor internals, and calculate the relative vibration of the plurality of reactor internals.

Further, the above relative vibration may be calculated based on detection time difference of the respective reflected waves. Furthermore, it is possible to process the reflected waves and calculate vibration displacement of the reflection surface.

Further, based on the reflected waveform formed by the respective reflected waves, a range of recording time of the reflected waveform may be decided. Furthermore, the ultrasonic waves may be transmitted by one pulse or a plurality of continuous pulses.

Further, with respect to the plurality of reactor internals vibrating relatively, a throat and diffuser of a jet pump, or a wedge and a bracket of the jet pump, or the throat and bracket of the jet pump are typical examples. Furthermore, it is possible to compare the calculated amplitude of the relative vibration with the threshold value obtained by a pre-analysis or by evaluation at the time of manufacture of the reactor internal and decide existence of abnormality.

Further, a reflection body may be installed at least on one reflection surface among the reflection surfaces of the plurality of reactor internals.

(1) A second feature of the present invention for attaining the above second object is a method of monitoring nuclear reactor vibration, comprising steps of transmitting ultrasonic waves from an ultrasonic sensor installed on an outer surface of a reactor pressure vessel toward an ultrasonic reflection member forming a plurality of ultrasonic reflection surfaces and installed at a vibration monitoring object position of an reactor internal in the reactor pressure vessel; receiving reflected waves generated at the respective reflection surfaces of the ultrasonic reflection member by the ultrasonic sensor; continuously recording the reflected waves by a signal process section; calculating moving amount of the reflected waves at each time of the continuously-recorded reflected waves by the signal process section; and measuring vibrational state at the monitoring object position from the moving amount of the reflected waves at each time.

When monitoring the vibrational state of the reactor internal in the reactor pressure vessel using ultrasonic waves by such a method, the reflected echoes from the monitoring object can be easily identified.

(2) In the above item (1), it is preferable to calculate the time difference of the respective reflected waves generated at the plurality of ultrasonic reflection surfaces, calculate sound speed of the ultrasonic waves in reactor water by using difference of ultrasonic propagation distance in the reactor water which is calculated based on time difference of the respective reflected waves and height difference of the plurality of ultrasonic reflection surfaces, and obtain the amplitude in the vibrational state at the monitoring object position.

(3) In the above item (1), it is preferable to decide a range of the recording time of the reflected waves by using the plurality of reflected waves generated at the plurality of ultrasonic reflection surfaces.

(4) In the above item (1), it is preferable that each of the ultrasonic reflection surfaces of the ultrasonic reflection plates is plane.

(5) In the above item (1), it is preferable that each of the ultrasonic reflection surfaces of the ultrasonic reflection plates is curved.

Advantageous Effect of the Invention

According to the first feature of the present invention, a minute relative vibration between reactor internals can be monitored to evaluate the soundness and abnormality of the reactor internals in the reactor pressure vessel.

According to the second feature of the present invention, when monitoring the vibrational state of the reactor internal in the reactor pressure vessel by using ultrasonic waves, the reflected echoes from the measurement object can be identified easily.

DETAILED DESCRIPTION OF THE PREFERRED EMBODIMENTS

Figure 1:
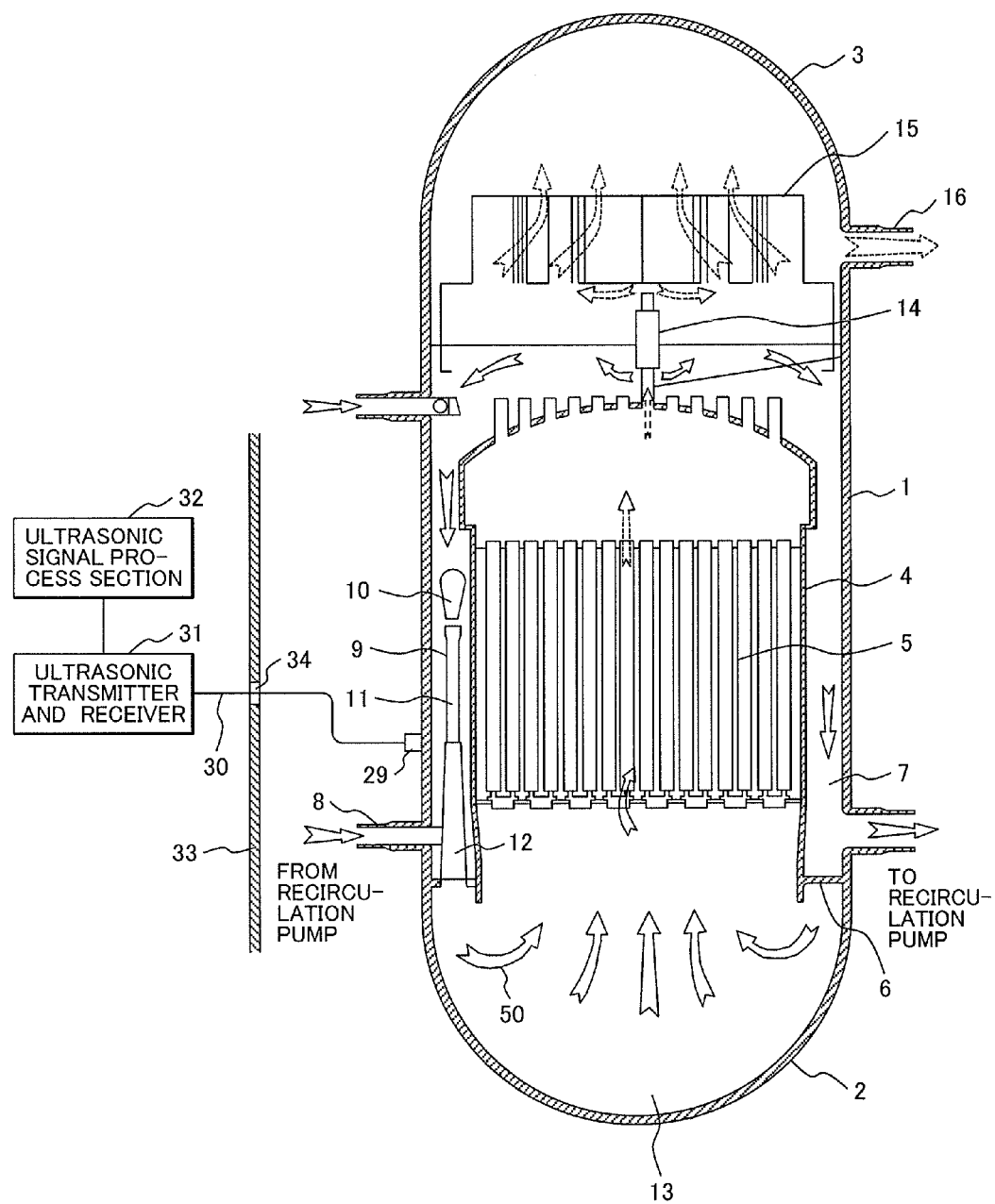
FIG. 1 is a structural diagram showing a nuclear reactor vibration monitoring apparatus applied to the boiling water reactor, according to embodiment 1 which is a preferable embodiment of the present invention.

Embodiments of the present invention will be explained below.

Embodiment 1

A nuclear reactor vibration monitoring apparatus of embodiment 1 which is a preferable embodiment of the present invention will be explained hereunder by referring to FIGS. 1 and 4. The nuclear reactor vibration monitoring apparatus of the present embodiment is used to monitor vibration of a jet pump installed in a reactor pressure vessel of a boiling water reactor.

The schematic structure of the boiling water reactor (BWR) will be explained below by referring to FIG. 1. The boiling water reactor is provided with a reactor pressure vessel (RPV) 1. The RPV 1 generally has an almost cylindrical shape, and one end thereof is closed by a bottom head 2, and the other end thereof is closed by a removable upper head 3. A core shroud 4 installed in the RPV 1 surrounds a core 5 disposed in the RPV 1. The core shroud 4 has an almost cylindrical shape and is supported by a ring shroud support member 6 installed in the RPV 1. An annular space (an annulus portion) 7 is formed between the RPV 1 and the core shroud 4.

An entrance nozzle 8 is extended through a side wall of the RPV 1 and is communicated with a nozzle 10 of a jet pump 9. A plurality of the jet pump 9 are disposed in the annulus portion 7 and attached to the shroud support member 6. Cooling water (a driving flow) in the RPV 1 pressurized by a recirculation pump (not drawn) disposed outside the RPV 1 is jetted from the nozzle 10 into a throat 11. By doing this, cooling water (a driven flow) in the annulus portion 7 is sucked into the throat 11. The driving flow and the driven flow are mixed in the throat 11 and are recovered to a static pressure by a diffuser 12 at the diffusion position. Cooling water (the driving flow and the driven flow) 50 discharged from the diffuser 12 is supplied to the core 5 through a lower plenum 13. By the installation of the jet pump 9, a larger quantity of cooling water than the quantity of cooling water sucked outside the RPV 1 by the recirculation pump can be supplied to the core 5. Furthermore, flow rate of the core 5 is controlled, thus using the change of the reactivity due to void effect (the effect that density of the cooling water is reduced due to generation of bubbles and the reactivity of the core is lowered) in the core 5, reactor power can be controlled. Steam generated by the core 5 is removed moisture by a steam separator 14 and a steam dryer 15 and is supplied to a turbine (not drawn) through a main steam nozzle 16. On the other hand, the cooling water separated by the steam separator 14 and the steam dryer 15 is mixed with feed water supplied to the RPV 1 by a feed water pipe (not drawn) in the annulus portion 7 and is supplied again to the core 5 by the jet pump 9.

Figure 2:
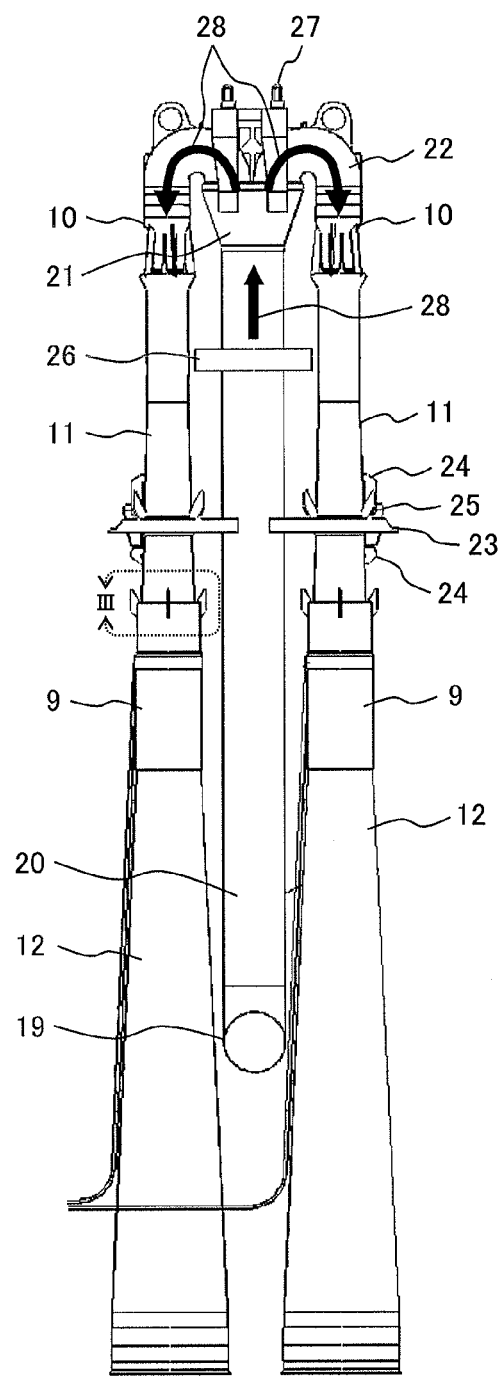
FIG. 2 is a structural diagram showing a jet pump shown in FIG. 1.
Figure 3:
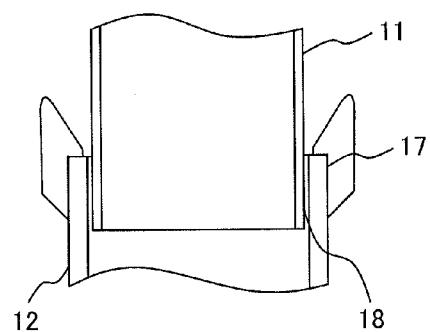
FIG. 3 is an enlarged vertical sectional view of a section III shown in FIG. 2.

By referring to FIGS. 2 and 3, the structure of the jet pump 9 will be explained. The jet pump 9 has the nozzle 10, the throat 11, and the diffuser 12. The nozzle 10 is disposed above the throat 11. The throat 11 and the diffuser 12 are connected to each other with a slip joint 17. A gap 18 is formed between the throat 11 and the diffuser 12. A lower end of the diffuser 12 is installed on the shroud support member 6. A riser elbow 19 connected to the recirculation pump passes through the RPV 1 and is connected to a riser pipe 20 disposed in the RPV 1. The riser pipe 20 is connected to the nozzle 10 via a transition piece 21 and an elbow 22. Numeral 23 indicates a bracket, 24 a support, 25 a wedge, and 26 a riser press. A driving flow 28 pressurized by the recirculation pump ascends through the riser pipe 20 and then reaches the nozzle 10 through the transition piece 21 and the elbow 22. When there is a pressure difference between the inside of the slip joint 17 and the outside thereof, the cooling water in the diffuser 12 leaks into the annulus portion 7 through the gap 18. Further, the driving flow 28 is changed in the flow direction by about 180° by the elbow 22. At this time, to oppose to the fluid reaction force applied to the elbow 22, a jet pump beam 27 (a beam) is attached.

The nuclear reactor vibration monitoring apparatus of the present embodiment is provided with an ultrasonic sensor 29, an ultrasonic transmitter and receiver 31, a coaxial cable 30, and an ultrasonic signal process section 32 for recording and processing an ultrasonic received waveform (see FIG. 1). The coaxial cable 30 is connected to an ultrasonic vibration element 35 of the ultrasonic sensor 29 and the ultrasonic transmitter and receiver 31. The ultrasonic signal process section 32 is connected to the ultrasonic transmitter and receiver 31. The ultrasonic sensor 29 includes the ultrasonic vibration element 35 and a front plate 36 arranged in front of the ultrasonic vibration element 35 as shown in FIG. 4.

Figure 4:
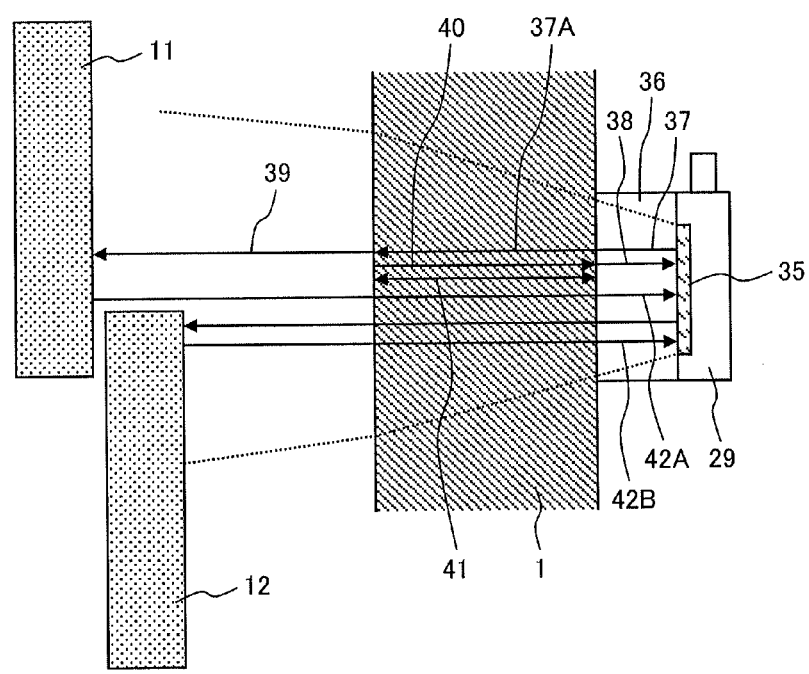
FIG. 4 is an explanatory drawing showing propagation paths of ultrasonic waves transmitted from an ultrasonic sensor of a nuclear reactor vibration monitoring apparatus shown in FIG. 1.

The ultrasonic sensor 29 is attached to the outer surface of the RPV 1 so as to effectively hit on the throat 11 and the diffuser 12 of the jet pump 9 which is an reactor internal in the RPV 1 where ultrasonic waves 39 vibrate relatively, as shown in FIG. 4. As a method of attaching the heat-resistant ultrasonic sensor 29, a method of installing it by clamping and pressurizing a soft metal such as gold, silver, or copper and a method for physically attaching it by a high-temperature adhesive, brazing, or high-temperature solder are known. If any method can transmit and receive ultrasonic waves stably even at a high temperature, any attaching art may be used. Further, when installing the ultrasonic sensor 29, it is possible to detect a plurality of ultrasonic reflected waves reflected from the throat 11 and the diffuser 12 and decide the installation position. Furthermore, it is possible to analyze beforehand the ultrasonic propagation path under each temperature condition by a simulation and decide the installation position of the ultrasonic sensor 29 in consideration of a difference between the temperature condition when the ultrasonic sensor 29 is installed and the temperature condition at the time of measurement, particularly, the sound speed change of the medium for the temperature change, and the expansion and contraction of the throat 11 and the diffuser 12 in correspondence with temperature change.

The ultrasonic sensor 29, concretely, the coaxial cable connected to the ultrasonic vibration element 35 is connected to the ultrasonic transmitter and receiver 31 through a wire pull-out hatch 34 of a reactor containment vessel 33 (refer to FIG. 1). In this state, ultrasonic waves 37 transmitted from the ultrasonic vibration element 35 of the ultrasonic sensor 29 toward the RPV 1 are reflected respectively from the throat 11 and the diffuser 12 through the RPV 1 and the cooling water (reactor water) in the annulus portion 7. The reflected waves (ultrasonic echoes) of the reflected ultrasonic waves 37 are received by the ultrasonic vibration element 35.

The received ultrasonic echoes are output from the ultrasonic sensor 29 as an electrical signal and is transferred to the ultrasonic transmitter and receiver 31 through the coaxial cable 30. The ultrasonic transmitter and receiver 31 stores the waveforms of the ultrasonic echoes on a time basis. Here, assuming that the throat 11 and the diffuser 12 vibrate horizontally toward the ultrasonic sensor 29, the propagation distance of the ultrasonic waves 37 changes on a time basis. Time position of the ultrasonic echoes (42A and 42B shown in FIG. 6 which will be described later) which are stored in the ultrasonic signal process section 32 on a time basis changes on an axis of time in correspondence with the respective vibrations of the throat 11 and the diffuser 12 (47A and 47B shown in FIG. 6). ½ of product of the difference on the axis of time between the two ultrasonic echoes 47A and 47B and the sound speed of the reactor water is equivalent to the relative distance between the throat 11 and the diffuser 12. Therefore, the change of the time difference is detected, thus the relative vibration (48 shown in FIG. 6) of the throat 11 and the diffuser 12 can be calculated. Further, the high-speed Fourier conversion (FFT) generally used is executed for each ultrasonic echo and the vibration waveform changing with time of the relative vibration waveforms (47A, 47B, and 48), thus frequency spectra of each vibration of the monitoring objects and the relative vibration of the monitoring objects can be obtained. The aforementioned is a basic operation principle of the method of monitoring nuclear reactor vibration of the present embodiment.

Next, the ultrasonic propagation path of the present embodiment will be described in detail by referring to FIG. 4. In the present embodiment, as a vibration monitoring object, that is, an ultrasonic reflection surface, for example, there are the respective outer surfaces of the throat 11 and the diffuser 12 of the jet pump 9. As other monitoring objects in the jet pump 9, there are the respective outer surfaces of the wedge 25 and the bracket 23 or the respective outer surfaces of the throat 11 and the bracket 23.

If the ultrasonic waves 37 are transmitted from the ultrasonic vibration element 35 of the ultrasonic sensor 29 to the respective outer surfaces (reflection surfaces) of the throat 11 and the diffuser 12, the ultrasonic waves 37 are propagated to the front plate 36 in the ultrasonic sensor 29 and are propagated to the RPV 1 as ultrasonic waves 37A at a transmission factor corresponding to the difference in the acoustic impedance (sound speed×density) between the front plate 36 and the RPV 1. Further, the ultrasonic waves 37 are reflected into the front plate 36, as reflected waves 38 at a reflection factor corresponding to the acoustic impedance. Similarly, the ultrasonic waves 37A propagated to the RPV 1 are divided into ultrasonic waves 39 to the reactor water and reflected waves 40 in the RPV 1. Here, since the difference in the acoustic impedance is large, the transmission factor from the RPV 1 to the reactor water is low such as about 5% at room temperature (3.5% at 300° C.) and the reflection factor is high such as 95% (96.5% at 300° C.). Therefore, the ultrasonic waves 37 transmitted from the ultrasonic sensor 29 are mostly multiple-reflected in the RPV 1. Accordingly, multiple reflected waves 41 may become noise as reverberation.

Furthermore, the ultrasonic waves 39 propagated in the reactor water reach the respective outer surfaces of the throat 11 and the diffuser 12. In the present embodiment, there exist the two reflection surfaces (the respective outer surfaces of the throat 11 and the diffuser 12), so that the reflected waves 42A and 42B from the two reflection surfaces are separated in time by the time corresponding to twice the distance between the two reflection surfaces in the horizontal direction and are received by the ultrasonic vibration element 35 through the reverse path of the ultrasonic propagation path aforementioned. In the present embodiment, for example, assuming that the ultrasonic vibration element 35 transmits only one wave (1 cycle of a sine wave (single pulse of the sine wave)) of the ultrasonic waves 37, the multiple reflected waves 41 in the RPV 1 are 1 cycle of the sine wave, though 1 cycle of the two reflected waves 42A and 42B which are sine waves shifted on the axis of time can be obtained as the respective reflected waves on the respective reflection surfaces of the throat 11 and the diffuser 12. Therefore, the ultrasonic signal process section 32 distinguishes only the reflected waves reflected on the respective reflection surfaces of the throat 11 and the diffuser 12 from ultrasonic signals including a plurality of reflected waves and can easily identify the waveforms of the recorded reflected waves.

Figure 5:
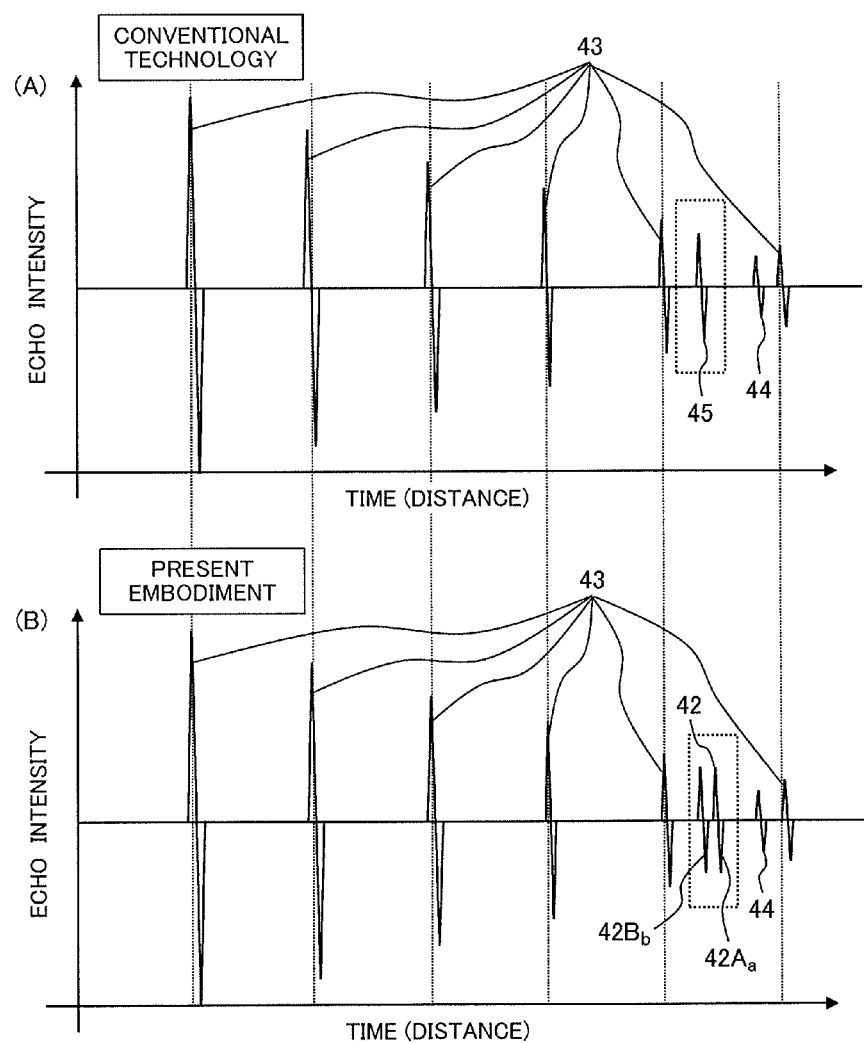
FIG. 5 is an explanatory drawing showing received waveform of ultrasonic waves received by an ultrasonic sensor of a nuclear reactor vibration monitoring apparatus shown in FIG. 1.

Difference in respective waveforms $42A_a$ and $42B_b$ of the reflected waves 42A and 42B and a method of deciding a waveform recording range will be explained below by referring to FIGS. 5 and 6. The ultrasonic sensor 29 transmits and receives ultrasonic waves, and the outline of all the waveforms recorded at that time is shown in FIG. 5 in comparison of the conventional technology ((A) of FIG. 5) with the present embodiment ((B) of FIG. 5). For the waveform of the received waves by the conventional technology, in the conventional technology of transmitting ultrasonic pulses to single reactor internal, receiving the reflected waves, and measuring the vibration displacement of the single reactor internal, the outline of all the waveforms when one wave of the ultrasonic waves 37 as in the present embodiment is transmitted is shown. Further, as shown in FIG. 5, in all the recorded waveforms, a plurality of waveforms 43 of the multiple reflected waves 41 in the RPV 1 are included and there exists a noise waveform 44 in correspondence with the shape echoes.

In the case of the conventional technology, since waveform 45 of a reflected wave from the monitoring object of the single reactor internal is processed, the reflected waveform is a waveform of one wave similarly to the waveforms 43 of the multiple reflected waves 41 and the noise waveform 44. Thus, it is difficult to identify the waveform 45 of the reflected waves from the reactor internal. Particularly, in a case where a reflection plate such as a corner reflector is installed, when the waveforms 43 and the noise waveform 44 of the multiple reflected waves are measured at a similar intensity to the reflected waveform from the single reactor internal, it is more difficult to identify the waveform 45. In addition, as aforementioned, if the temperatures of the RPV 1 and the reactor water to which ultrasonic waves are propagated are changed, the respective sound speeds in the RPV 1 and the reactor water are changed. Therefore, the time position of the waveform 45 of the necessary reflected wave moves on the axis of time and it is more and more difficult to identify the waveform 45.

On the other hand, when the respective reflected waves from the reflection surfaces (the respective reflection surfaces of the throat 11 and the diffuser 12) of the two reactor internals in the present embodiment are used, as shown in FIG. 5, the respective waveforms 42 for the reflected waves 42A and 42B from the respective reflection surfaces of the two reactor internals are obtained. As aforementioned, the time interval between the two reflected waves 42A and 42B is equivalent to twice the distance in the horizontal direction between the two reflection surfaces. Further, although the noise waveform 44 in correspondence with the above multiple reflected waveforms 43 and the above shape echoes in the RPV 1 is an independent single pulse, the waveform 42 of the reflected waves (the reflected waves on the respective reflection surfaces of the throat 11 and the diffuser 12) in the present embodiment is paired pulses having fixed intervals on the axis of time and is different in the waveform itself from the multiple reflected waveforms 43 and the noise waveform 44, so that it can be identified easily. Furthermore, even if the positions of the waveforms 42 (the waveforms $42A_a$ and $42B_b$ shown in FIG. 5) of the two reflected waves 42A and 42B on an axis of time are changed due to the sound speed change of the medium in correspondence with the temperature change, the waveforms 42 can be easily identified so long as the multiple reflected waves and noise waves do not interfere with each other. Further, the shape echo means a reflected wave at a corner of the reflection surface of the reactor internal.

In the present embodiment, an example of transmission of one wave (single pulse) of ultrasonic waves is shown, though in addition to one wave, two or more waves of ultrasonic waves may be transmitted. In short, by one transmission of ultrasonic waves, if any number of waves permits the waveforms of the respective reflected waves reflected on the respective reflection surfaces of the two reactor internals to become paired waveforms, it is acceptable. Even in the case of a plurality of waves, the waveform of reflected waves by the conventional technology is a waveform of a plurality of waves similarly to the multiple reflected waveforms 43 and the noise waveform 44 and it is difficult to identify the waveform 45 of the reflected waves from the reactor internal. Qualitatively, as the interval between the two reactor internals becomes narrower, fewer waveforms are preferable.

Figure 6:
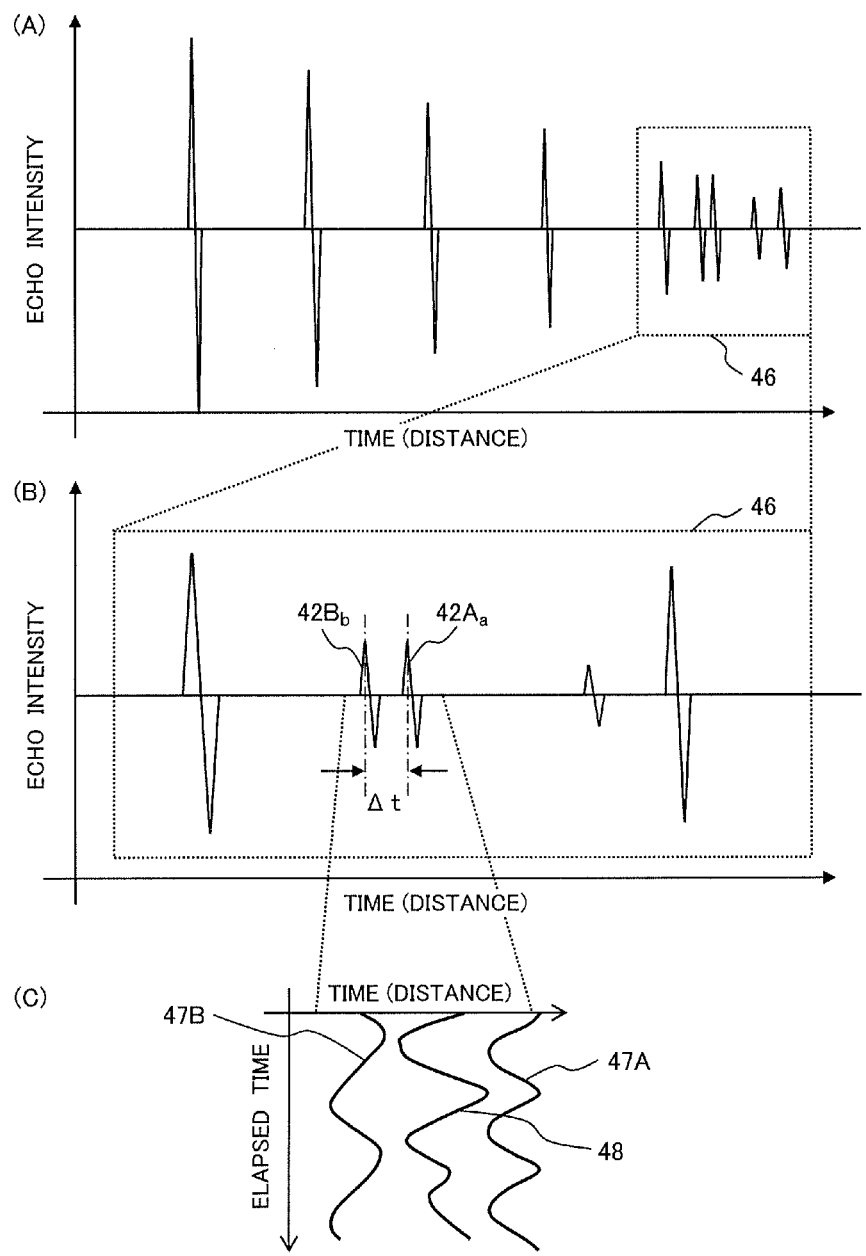
FIG. 6 is an explanatory drawing showing setting of an ultrasonic recording range and a vibration measuring method according to a nuclear reactor vibration monitoring apparatus shown in FIG. 1.

As aforementioned, after the waveforms 42 of the reflected waves including the two reflected waves 42A and 42B are identified, as shown in (A) and (B) of FIG. 6, an ultrasonic recording range 46 is set within a range including the two reflected waves 42A and 42B and the waveforms are recorded on a time basis. In this case, if the monitoring objects (the throat 11 and the diffuser 12) vibrate, only the waveform $42A_a$ of the reflected waves 42A and the waveform $42B_b$ of the reflected waves 42B, that is, only the waveforms 42 of the reflected waves move right and left in correspondence with the vibration on the axis of time. The changes with time of the waveform $42A_a$ of the reflected waves 42A and the waveform $42B_b$ of the reflected waves 42B are respectively shown by 47A and 47B in (C) of FIG. 6.

The distance ΔH in the horizontal direction between the two reflection surfaces is obtained by substituting the distance ΔH in the horizontal direction between the two reflection surfaces into Formula (1). The relative vibration can be obtained by calculating a change with time of the distance ΔH. The change with time of the relative vibration is shown by 48 in (C) of FIG. 6.

$$\Delta H(t) = Vw \times \Delta t/2 \quad (1)$$

Further, after the distances from the two reflection surfaces are obtained based on the arrival time, the amplitude of the relative vibration can be obtained as a difference between the distances.

The amplitude of the relative vibration is monitored, thus abnormality such as a reduction in the plate thickness due to wear of reflected waves and changes in the vibration state due to the change with time can be measured. By comparing the amplitude of the relative vibration with the threshold value obtained by a pre-analysis or by evaluation at the time of manufacture of the reactor internal in the RPV 1, the vibration state can be evaluated.

In addition, ultrasonic waves are transmitted respectively from a plurality of ultrasonic sensors installed on the outer surface of the RPV 1 to the two reactor internals in the reactor, and the vibrations of the reactor internals in the RPV 1 are measured. By obtaining a difference between the vibrations of the reactor internals, the relative vibration can be measured. However, the propagation paths and intensities of the respective ultrasonic waves transmitted from the respective ultrasonic sensors and a reduction in the accuracy due to the characteristics of the delay member are worried. On the other hand, according to the present embodiment, the two reflected waves are received by one ultrasonic sensor 29, so that the reduction in the accuracy due to the differences in the ultrasonic propagation path and the ultrasonic sensor can be suppressed and measurement with high precision can be realized.

In the present embodiment, an example that the transmitted ultrasonic waves are a sine wave is explained, though the ultrasonic waves may be a pulse having a pointed edge or a square wave or a triangular wave. In short, by one transmission of ultrasonic waves, if any waveform permits the waveforms of the reflected waves reflected from the reflection surfaces of the two reactor internals to become paired waveforms, it is acceptable. Qualitatively, as the interval between the two apparatuses becomes narrower, a pointed-edge shape is preferable.

Further, in the above explanation, the monitoring object apparatus having curved reflection surfaces is subjected, though when a detection signal of the reflected waves is small, for the reflection surfaces, a reflection body such as a reflection plate or a corner reflector may be used.

Embodiment 2

A method of monitoring nuclear reactor vibration according to embodiment 2 which is another preferable embodiment of the present invention will be explained hereunder by referring to FIGS. 7 and 8. The method of monitoring nuclear reactor vibration according to the present embodiment monitors the vibration of the jet pump being the reactor internal installed in the RPV 1 of the boiling water reactor.

Figure 7:
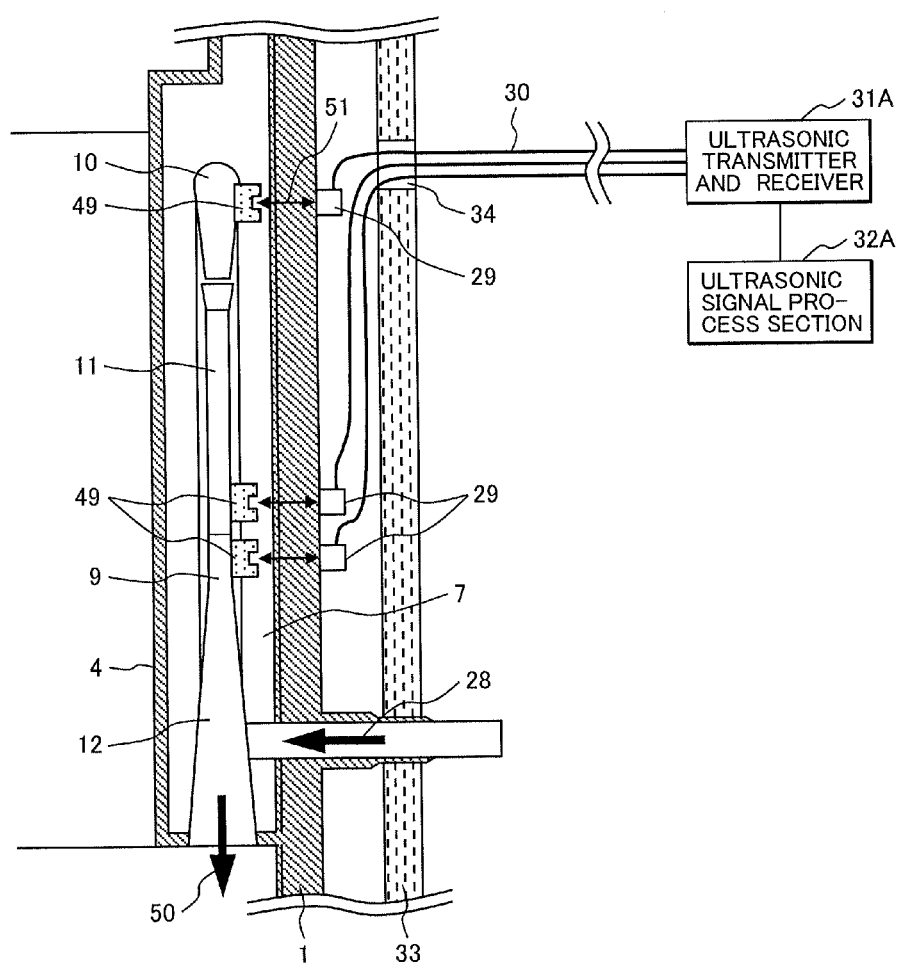
FIG. 7 is a structural diagram showing a nuclear reactor vibration monitoring apparatus used in a method of monitoring nuclear reactor vibration according to embodiment 2 which is another preferable embodiment of the present invention.

The method of monitoring nuclear reactor vibration according to the present embodiment uses the nuclear reactor vibration monitoring apparatus shown in FIG. 7. The nuclear reactor vibration monitoring apparatus is provided with an ultrasonic reflection plate 49, the ultrasonic sensor 29, an ultrasonic transmitter and receiver 31A, the coaxial cable 30, and an ultrasonic signal process section 32A for recording and processing an ultrasonic received waveform. The coaxial cable 30 is connected to the ultrasonic vibration element 35 of the ultrasonic sensor 29 and the ultrasonic transmitter and receiver 31A. The ultrasonic signal process section 32A is connected to the ultrasonic transmitter and receiver 31A. The structure of the ultrasonic sensor 29 is the same as that of the ultrasonic sensor 29 used in embodiment 1.

Three ultrasonic reflection plates 49 are attached to the jet pump 9. The respective ultrasonic reflection plates 49 are attached to the respective outer surfaces of the nozzle 10, the throat 11, and the diffuser 12 and face an inner surface of the RPV 1. The attaching places of the ultrasonic reflection plates 49 are the monitoring object portions of the jet pump 9. The detailed structure of the ultrasonic reflection plates 49 will be described later by referring to FIG. 8. With respect to the attaching method of the ultrasonic reflection plates 49, any attaching method resistant over a long period of time to temperature change and vibration such as screwing, fixing jigging, and welding to a monitoring object position is acceptable.

The ultrasonic sensor 29 is attached at the position of the outer surface of the RPV 1 where ultrasonic waves 51 are efficiently hit on the ultrasonic reflection plates 49. The attachment of the ultrasonic sensor 29 on the outer surface of the RPV 1 is executed similarly to Embodiment 1.

The coaxial cable 30 connected to the ultrasonic sensor 29 is connected to the ultrasonic transmitter and receiver 31A through the wire pull-out hatch 34 of the reactor containment vessel 33. In this state, ultrasonic waves 51 are transmitted from the ultrasonic vibration element 35 of the ultrasonic sensor 29 toward the RPV 1 and are reflected from the respective ultrasonic reflection plates 49 via the RPV 1 and the reactor water in the annulus portion 7. The reflected echoes reflected on the ultrasonic reflection plates 49 are received by the ultrasonic vibration element 35 of the ultrasonic sensor 29. The received ultrasonic echoes are output from the ultrasonic sensor 29 as an electrical signal and are input to the ultrasonic transmitter and receiver 31A through the coaxial cable 30. The ultrasonic transmitter and receiver 31A stores the waveforms of the ultrasonic echoes on a time basis. Here, assuming that the jet pump 9 vibrates horizontally toward the ultrasonic sensor 29, the propagation distance of the ultrasonic waves 51 changes on a time basis. The time position of the reflected echoes which are stored in the ultrasonic signal process section 32A on a time basis changes on the axis of time in correspondence with the above vibration of the jet pump 9. If the change in the reflected echoes on the axis of time is detected, the vibration at the monitoring object position is measured. The change with time of the reflected echoes and the sound speed of the reactor water at the monitoring object position are multiplied, thus an absolute value of the vibration amplitude can be obtained. Further, for the vibration waveform changed with time, the high-speed Fourier conversion (FFT) generally used is executed, thus frequency spectra of the vibration of the monitoring object can be obtained.

Next, by referring to FIG. 8, the structure of the ultrasonic reflection plates 49 and the ultrasonic propagation path will be explained in detail.

Figure 8:
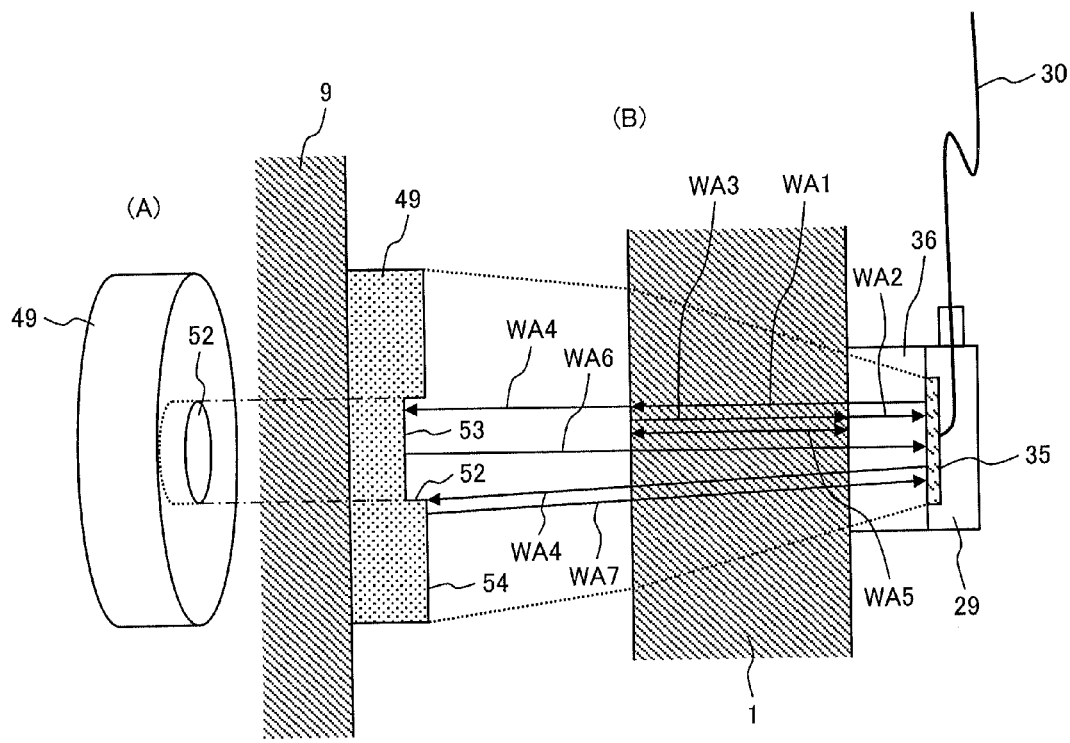
FIG. 8 is an explanatory drawing showing a method of monitoring nuclear reactor vibration according to embodiment 2 using a nuclear reactor vibration monitoring apparatus shown in FIG. 7.

The ultrasonic reflection plate 49 (see (B) of FIG. 8) attached to the outer surface of the jet pump 9 has a shape of a disc and forms a circular hollow 52 at its center as shown in (A) of FIG. 8. The ultrasonic reflection plate 49 forms reflection surfaces 53 and 54 for reflecting ultrasonic waves. The reflection surfaces 53 and 54 are parallel to each other and the reflection surface 53 is the bottom of the hollow 52. The reflection surface 54 is positioned on the side of the RPV 1 instead of the reflection surface 53.

When the ultrasonic waves 51 are transmitted from the ultrasonic sensor 29 toward the ultrasonic reflection surface 49, the ultrasonic waves 51 are propagated to the front plate 36 inside the ultrasonic sensor 29. The ultrasonic waves 51 are propagated to the RPV 1 as ultrasonic waves WA1 at a transmission factor corresponding to the difference in the acoustic impedance (sound speed×density) between the front plate 36 and the RPV 1 and are reflected into the front plate 36 as reflected waves WA2 at a reflection factor corresponding to the acoustic impedance. Similarly, the ultrasonic waves WA1 propagated to the RPV 1 are divided into ultrasonic waves WA4 propagated to the reactor water and reflected waves WA3 into the RPV 1. Here, since the difference in the acoustic impedance is large, the transmission factor from the RPV 1 to the reactor water is low such as about 5% at room temperature (3.5% at 300° C.) and the reflection factor is high such as 95% (96.5% at 300° C.). Therefore, the ultrasonic waves 51 transmitted from the ultrasonic sensor 29 are mostly multiple-reflected in the RPV 1. Therefore, multiple reflected waves WA5 may become noise as reverberation.

Furthermore, the ultrasonic waves WA4 propagated in the reactor water reach the reflection plate 49 and are reflected respectively from the reflection surfaces 53 and 54. Reflected waves WA6 from the reflection surface 53 and reflected waves WA7 from the reflection surface 54 are received by the ultrasonic vibration element 35 of the ultrasonic sensor 29 via the reverse path of the ultrasonic propagation path aforementioned. Since the two reflection surfaces 53 and 54 are formed on the reflection plate 49, the reflected waves WA6 reach the ultrasonic vibration element 35 later than the reflected waves WA7 by the time corresponding to twice the distance difference between the distance from the inner surface of the RPV 1 in the horizontal direction to the reflection surface 53 and the distance from the inner surface of the RPV 1 in the horizontal direction to the reflection surface 54, that is, to the distance going back and forth on the distance in the horizontal direction between the reflection surface 53 and the reflection surface 54.

In the present embodiment, the two reflection surfaces 53 and 54 are formed on each of the reflection plates 49 attached to the outer surface of the jet pump 9, so that the two reflected waves WA6 and WA7 shifted by the time equivalent to twice the distance in the horizontal direction between the reflection surface 53 and the reflection surface 54 are obtained. For example, assuming that one wave (1 cycle of a sine wave) of the ultrasonic waves is transmitted, similarly to embodiment 1, the multiple reflected waves WA5 in the RPV 1 are 1 cycle of the sine wave, though the reflected waves WA6 and WA7 from the reflection surfaces 53 and 54 are 1 cycle of the sine waves mutually shifted on the axis of time. Therefore, the ultrasonic signal process section 32 can distinguish only the reflected waves WA6 and WA7 reflected on the reflection plate 49 from ultrasonic signals including a plurality of reflected waves and can easily identify the waveforms of the recorded reflected waves.

Next, by referring to FIGS. 9 and 10, the waveform of ultrasonic waves measured by the method of monitoring nuclear reactor vibration according to the present embodiment will be explained.

Figure 9:
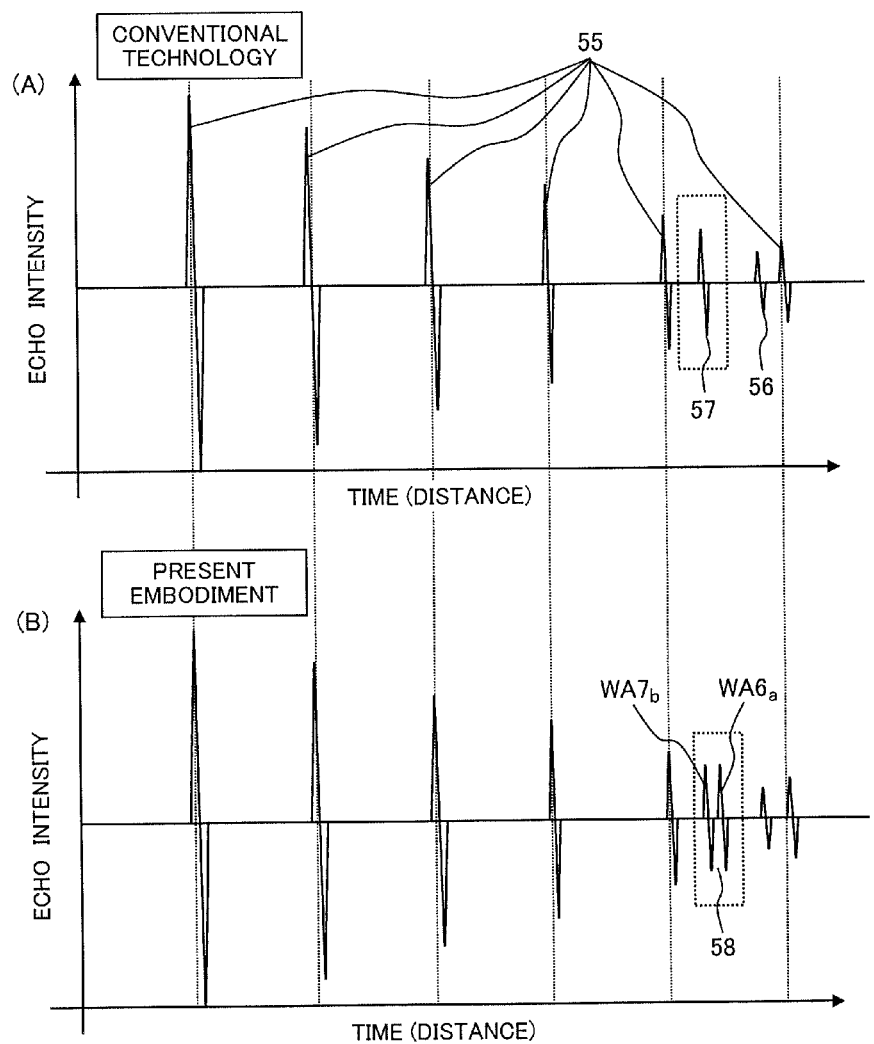
FIG. 9 is an explanatory drawing showing received waveform of ultrasonic waves received by an ultrasonic sensor of the nuclear reactor vibration monitoring apparatus shown in FIG. 7.

The ultrasonic sensor 29 transmits and receives ultrasonic waves and the outline of all the waveforms recorded at that time is shown in FIG. 9 in comparison of the conventional technology with the present embodiment.

(A) of FIG. 9 shows the waveforms of ultrasonic waves measured using the conventional reflection plate attached to the outer surface of the jet pump 9. The conventional reflection plate is the corner reflector described in Japanese Patent 4551920.

As shown in (A) of FIG. 9, a plurality of waveforms 55 of the multiple reflected waves WA5 in the RPV 1 are included in all the waveforms recorded and there exist noise waveforms 56 in correspondence with the shape echoes. In the case of the conventional technology, the reflection plate uses a corner reflector made up of a plane, so that the waveform of reflected waves is a waveform similar to the multiple reflected wave 55 and the noise waveform 56. Therefore, particularly, when these waveforms are measured at a similar-level intensity, it is difficult to identify a waveform 57 of reflected waves from the conventional reflection plate installed at the monitoring object position. Furthermore, as aforementioned, if the temperatures of the RPV 1 and the reactor water to which ultrasonic waves are propagated are changed, the respective sound speeds are also changed, so that the time position of the waveform 57 of reflected wave moves on the axis of time and the identification of the waveform 57 is more and more difficult.

On the other hand, in the present embodiment using the reflection plate 49, as shown in (B) of FIG. 9, waveforms 58 (the waveforms WA6$_a$ and WA7$_b$) of the two reflected waves from each of the reflection plate 49 can be obtained. The time interval of the waveforms WA6$_a$ and WA7$_b$ of the two reflected waves, as aforementioned, is equivalent to the time required for ultrasonic waves to move on the distance twice the distance in the horizontal direction between the reflection surface 53 and the reflection surface 54. Further, the waveform WA6$_a$ of the reflected waves WA6 and the waveform WA7$_b$ of the reflected waves WA7 are different in the waveform itself from the multiple reflected wave 55 and the noise waveform 56 in correspondence with the shape echoes in the RPV 1 which are aforementioned, so that the identification of the waveforms WA6$_a$ and WA7$_b$ can be performed easily. Furthermore, even if the position of the waveforms 58 of the two reflected waves is changed due to the sound speed change of the medium in correspondence with the temperature change, the waveforms 58 can be easily identified so long as the multiple reflected waves and noise waves do not interfere with each other.

Figure 10:
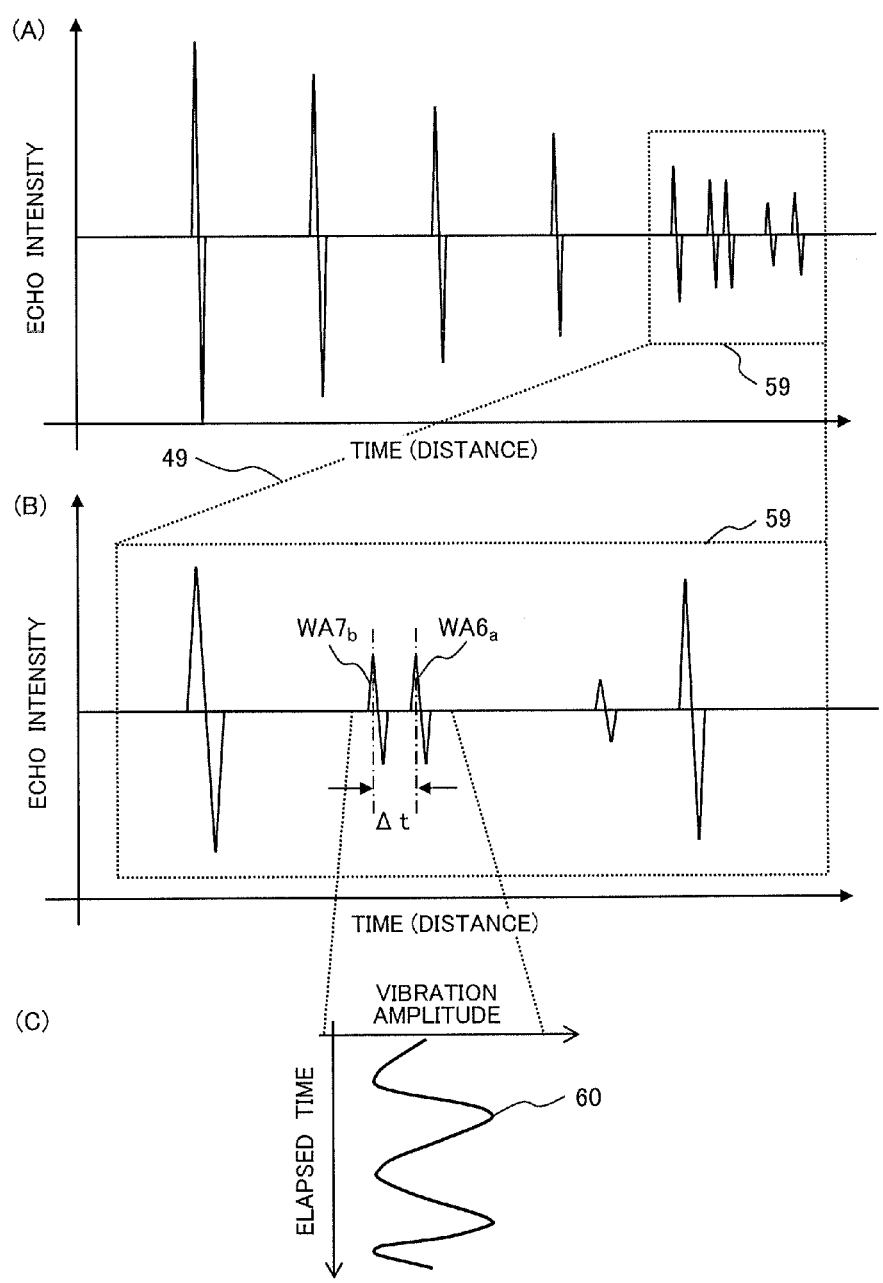
FIG. 10 is an explanatory drawing showing a method of deciding a waveform recording range of measured waveform by a method of monitoring nuclear reactor vibration according to embodiment 2.

Furthermore, after the waveforms WA6$_a$ and WA7$_b$ of the two reflected waves are identified, as shown in FIG. 10, an ultrasonic recording range 59 is set within the range including the waveforms and the waveforms are recorded on a time basis. Further, (B) of FIG. 10 shows the waveform when the ultrasonic recording range 59 shown in (A) of FIG. 10 is recorded.

In this case, if the monitoring object vibrates, only the waveforms WA6$_a$ and WA7$_b$ of the two reflected waves move right and left on the axis of time in correspondence with the vibration amplitude. Further, when obtaining the amplitude, using the time difference Δt of the waveforms of the two reflected waves and the distance between the two reflection surfaces (the distance in the horizontal direction between the reflection surface 53 and the reflection surface 54) ΔH in the horizontal direction, the sound speed Vw of the reactor water at the monitoring object position can be obtained by Formula (1) aforementioned.

When obtaining the vibration amplitude at the monitoring object position, the time moving amount of the waveform of the reflected waves measured at each time is multiplied by the sound speed of the reactor water indicated by Formula (1), thus a vibration amplitude 60 (refer to (C) of FIG. 10) can be obtained with higher precision than the conventional technology. Here, if the jet pump 9 vibrates, depending on the vibration, the waveform of the reflected waves measured is watched to move on the axis of time, so that the moving amount is the moving amount of the reflected waveform aforementioned. Further, in addition to the amplitude, the vibration state such as the frequency and vibration mode can be evaluated.

Next, the dimensions of the reflection plates used in the method of monitoring nuclear reactor vibration according to the present embodiment will be explained by referring to FIG. 11.

Figure 11:
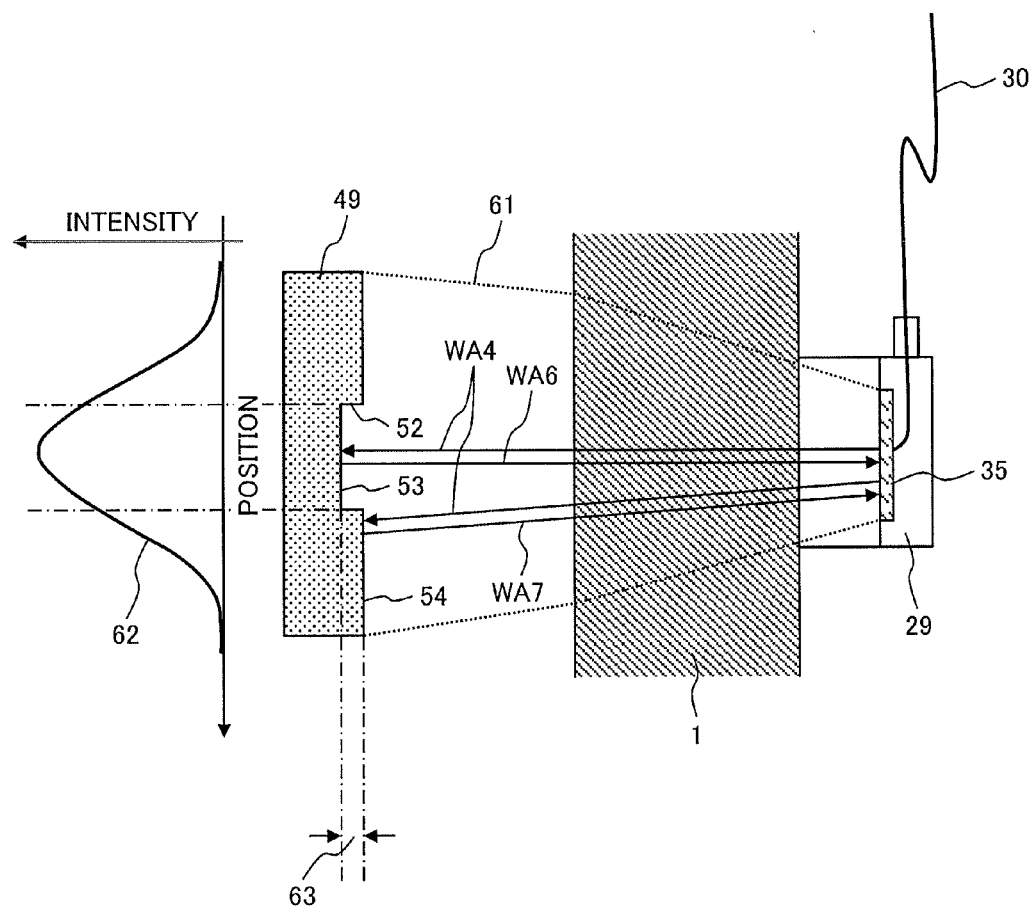
FIG. 11 is an explanatory drawing showing dimensions of a reflection plate used in a method of monitoring nuclear reactor vibration according to embodiment 2.

With regard to the dimensions (the outer diameter of the reflection plate 49 and the inner diameter of the hollow 52) of the reflection plate 49 attached to the outer surface of the jet pump 9, as shown in FIG. 11, the respective dimensions of the reflection surfaces 53 and 54 are decided in such a way that the intensities of the two reflected waves WA6 and WA8 received by the ultrasonic sensor 29 become to the same extent based on a spread 61 of ultrasonic waves transmitted from the ultrasonic sensor 29 and an intensity distribution 62 of ultrasonic waves on the reflection plate 49, by a simulation. If the ultrasonic vibration element 35 is circular, the analytical method of the spread 61 of ultrasonic waves and the intensity distribution 62 thereof obtains a Vessel function type intensity distribution. This is described in detail in a technical journal, so that the explanation thereof will be omitted. Further, a distance 63 in the horizontal direction between the reflection surface 53 and the reflection surface 54 is set to a distance that allows for a time difference for avoiding mutual interference of the two reflected echoes, in consideration of the frequency and the number of waves of the ultrasonic sensor 29 used for measurement and the transmission system (a single pulse, burst).

As explained above, according to the present embodiment, in the vibration measurement of the reactor internal including the jet pump 9 in the boiling water reactor, the ultrasonic reflection plates 49 made up of two or more planes or curved surfaces are installed at the monitoring object position, thus the two characteristic reflected waves WA6 and WA7 are generated, and these reflected waves are received, thereby these reflected waves can be distinguished from the multiple reflected echoes in the RPV 1, the noise echoes generated by the spread 61 of ultrasonic waves, and the shape echoes and identified. Therefore, the ultrasonic recording range can be set without executing a correction by the propagation distance of each medium and the sound speed in consideration of the sound speed change of the ultrasonic propagation medium due to the temperature change and the relative position shift due to the temperature change. Further, the sound speed Vw of ultrasonic waves of the reactor water at the temperature at the time of measurement is obtained based on the time difference Δt between the two reflected waves WA6 and WA7 and the distance ΔH in the horizontal direction between the reflection surface 53 and the reflection surface 54, and the amplitude in the vibration state at the monitoring object position is corrected, thus the vibration amplitude can be obtained with high precision.

Therefore, in the present embodiment, when monitoring the vibration state of the reactor internal (for example, the jet pump 9) in the RPV 1 using ultrasonic waves, the reflected echoes from the monitoring object can be identified easily.

Embodiment 3

Figure 12:
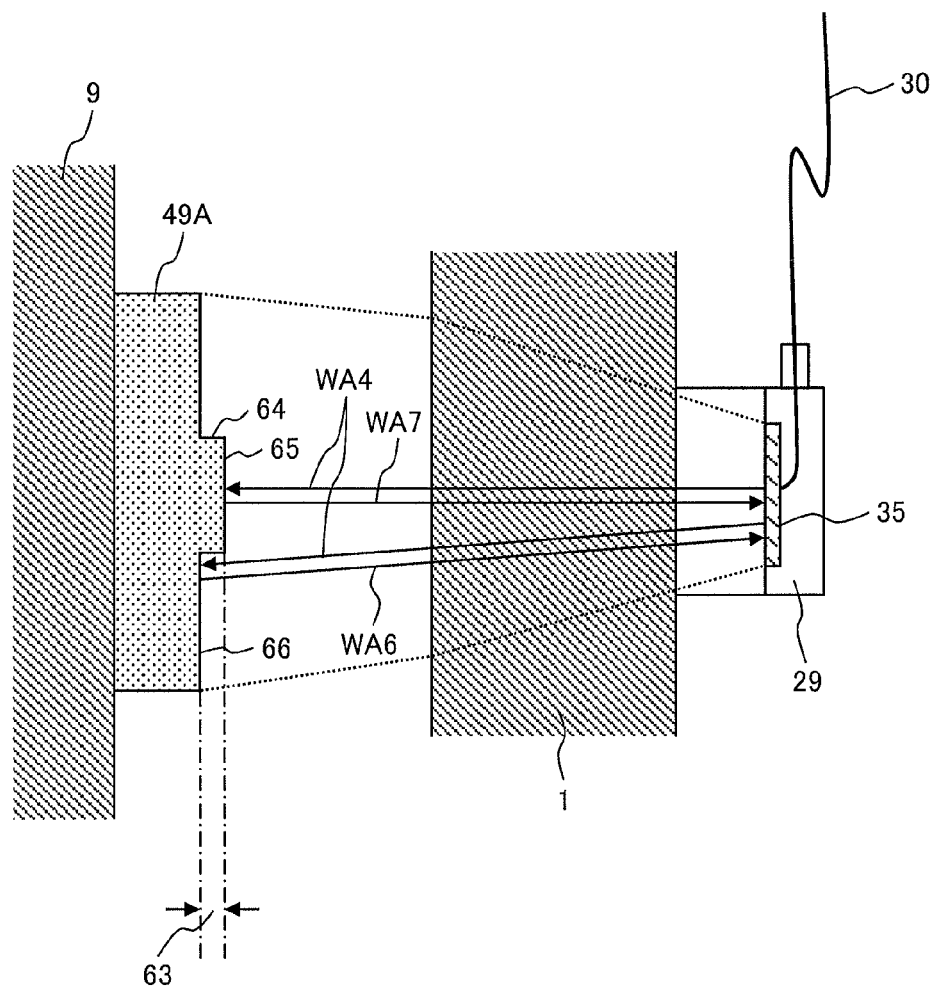
FIG. 12 is an explanatory drawing showing shape of a reflection plate used in a method of monitoring nuclear reactor vibration according to embodiment 3 which is another preferable embodiment of the present invention.

A method of monitoring nuclear reactor vibration according to embodiment 3 which is another preferable embodiment of the present invention will be explained hereunder by referring to FIG. 12. The method of monitoring nuclear reactor vibration according to the present embodiment monitors the vibration of the jet pump being the reactor internal installed in the RPV 1 of the boiling water reactor.

In the method of monitoring nuclear reactor vibration according to the present embodiment, an ultrasonic reflection plates 49A is used instead of the ultrasonic reflection plates 49 used in embodiment 2 and a plurality of ultrasonic reflection plates 49A, similarly to embodiment 2, are attached to the outer surface of the jet pump 9. The ultrasonic reflection plate 49A has a shape that a projection 64 with a circular section on the surface facing the inner surface of the RPV 1 is formed. Due to the formation of the projection 64, two parallel reflection surfaces 65 and 66 are formed in the ultrasonic reflection plate 49A. The reflection surface 65 is formed at the leading edge of the projection 64 and the reflection surface 66 is formed on the ultrasonic reflection plate 49A at the base of the projection 64. The reflection surfaces 65 and 66 perform the similar function to the reflection surfaces 53 and 54 in embodiment 2. The waveforms $WA6_a$ and $WA7_b$ of the respective reflected waves WA6 and WA7 from the reflection surfaces 65 and 66 which are generated by the ultrasonic waves 51 transmitted from the ultrasonic sensor 29 set on the outer surface of the RPV 1 are identified and can be measured on a time basis, thus the vibration at the monitoring object position can be measured. Further, the sound speed of the reactor water at that time is measured based on the time difference between the reflected wave WA6 and the reflected wave WA7 which are received and the distance in the horizontal direction between the reflection surface 66 and the reflection surface 65, so that in the present embodiment, the vibration amplitude at the monitoring object position can be obtained with higher precision than the conventional technology.

Also in the present embodiment, when monitoring the vibration state of the reactor internal in the RPV 1 using ultrasonic waves, the reflected echoes from the monitoring object can be identified easily.

Embodiment 4

Figure 13:
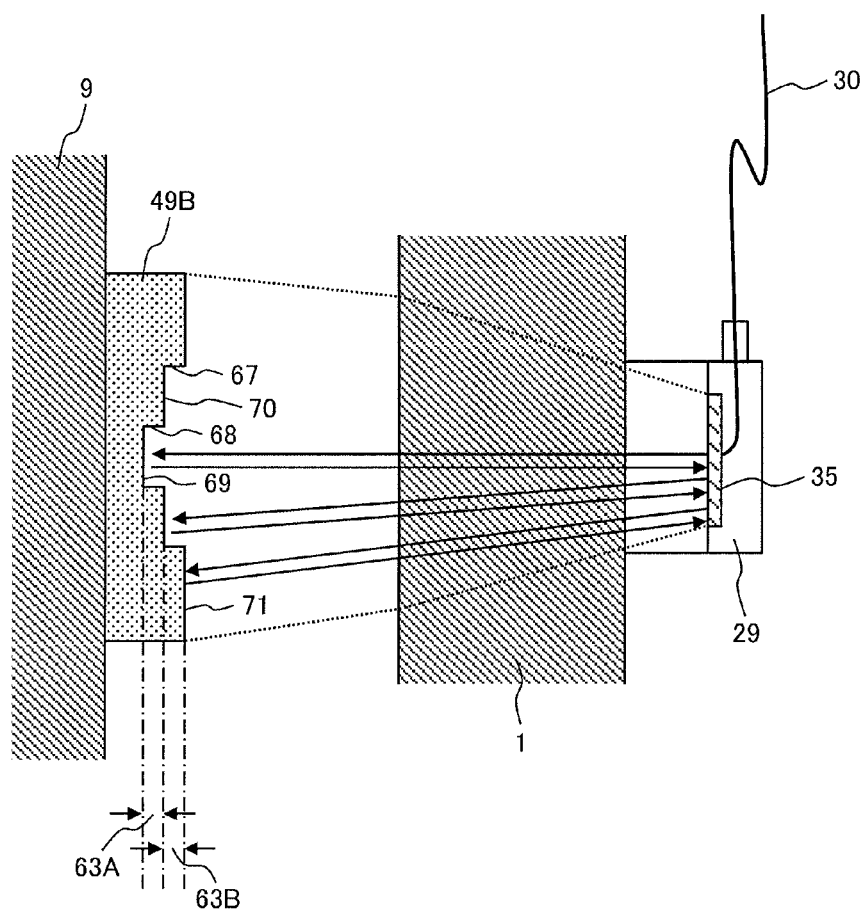
FIG. 13 is an explanatory drawing showing shape of a reflection plate used in a method of monitoring nuclear reactor vibration according to embodiment 4 which is another preferable embodiment of the present invention.

A method of monitoring nuclear reactor vibration according to embodiment 4 which is another preferable embodiment of the present invention will be explained hereunder by referring to FIG. 13. The method of monitoring nuclear reactor vibration according to the present embodiment monitors the vibration of the jet pump being the reactor internal installed in the RPV 1 of the boiling water reactor.

In the method of monitoring nuclear reactor vibration according to the present embodiment, an ultrasonic reflection plates 49B is used instead of the ultrasonic reflection plates 49 used in embodiment 2 and a plurality of ultrasonic reflection plates 49B, similarly to embodiment 2, are attached to the outer surface of the jet pump 9. The ultrasonic reflection plate 49B forms a hollow 67 on the surface facing the inner surface of the RPV 1 and forms another hollow 68 on the bottom of the hollow 67. As a result, a reflection surface 69 which is the bottom of the hollow 68, a reflection surface 70 which is the bottom of the hollow 67, and a reflection surface 71 which is the surface of the ultrasonic reflection plate 49B are formed in parallel with each other on the ultrasonic reflection plate 49B. Depth of the hollow 68, that is, a distance in the horizontal direction between the reflection surface 69 and the reflection surface 70 is "63A" and depth of the hollow 67, that is, a distance in the horizontal direction between the reflection surface 70 and the reflection surface 71 is "63B". When the respective ultrasonic waves from the reflection surfaces 69, 70, and 71 which are generated by the ultrasonic waves 51 transmitted from the ultrasonic sensor 29 set on the outer surface of the RPV 1 are received, in the three combinations of the reflection surfaces which are paired among the reflection surfaces 69, 70, and 71, the sound speed of the reactor water is obtained based on the distance in the horizontal direction between the two reflection surfaces in each combination and the difference in the reception time of the two reflected waves reflected from the two reflection surfaces, and the mean value of the sound speeds of the reactor water obtained by the three combinations of the reflection surfaces is obtained. The mean value of these sound speeds is obtained, thus the vibration amplitude at the monitoring object position can be obtained with higher precision than the conventional technology. However, if the number of wave reflection surfaces increases, depending on the number of divisions, the echo intensities of the respective reflected waves are lowered, so that the number of reflection surfaces must be selected within the range for keeping a sufficient echo intensity.

Also in the present embodiment, when monitoring the vibration state of the reactor internal in the RPV 1 using ultrasonic waves, the reflected echoes from the monitoring object can be identified easily.

Embodiment 5

Figure 14:
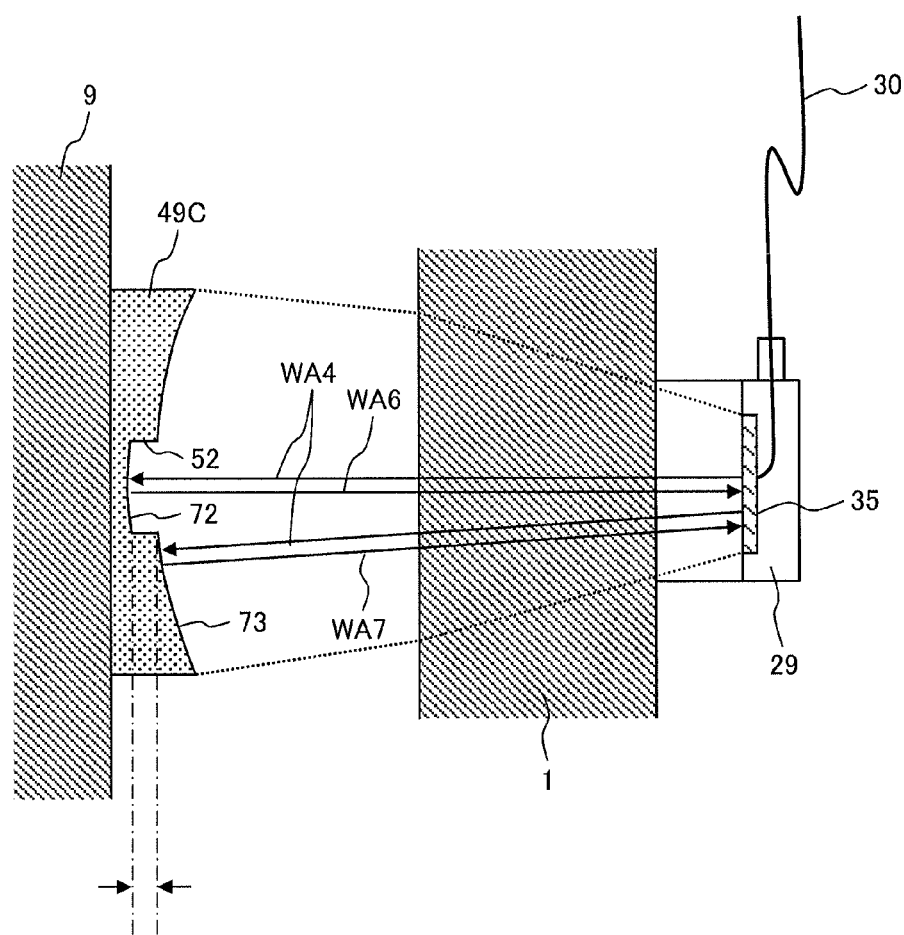
FIG. 14 is an explanatory drawing showing shape of a reflection plate used in a method of monitoring nuclear reactor vibration according to embodiment 5 which is another preferable embodiment of the present invention.

A method of monitoring nuclear reactor vibration according to embodiment 5 which is another preferable embodiment of the present invention will be explained hereunder by referring to FIG. 14. The method of monitoring nuclear reactor vibration according to the present embodiment monitors the vibration of the jet pump being the reactor internal installed in the RPV 1 of the boiling water reactor.

In the method of monitoring nuclear reactor vibration according to the present embodiment, an ultrasonic reflection plates 49C is used instead of the ultrasonic reflection plates 49 used in embodiment 2 and a plurality of ultrasonic reflection plates 49C, similarly to embodiment 2, are attached to the outer surface of the jet pump 9. The ultrasonic reflection plate 49C includes reflection surfaces 72 and 73 in a reflection lens shape with the reflection surfaces 53 and 54 curved. The reflection surfaces 72 and 73 function similarly to the reflection surfaces 53 and 54. The reflection surfaces 72 and 73 have a reflection lens shape, so that the intensity reduction of the reflected waves due to diffusion of the reflected wave from each reflection surface can be prevented and the intensity can be kept high. Therefore, the vibration amplitude of the jet pump 9 can be measured at a high SN ratio (signal to noise ratio). For the shape of the reflection surfaces 72 and 73 in a lens shape, as shown also in FIG. 11, a focal distance may be set in consideration of the spread of ultrasonic waves transmitted from the ultrasonic sensor 29 and the respective focal distances of the reflection surfaces 72 and 73 may be set so as to be almost the same. Further, also in this case, the sound speed of the reactor water at that time is obtained based on the time difference between the reflected wave WA6 and the reflected wave WA7 which are received and the distance in the horizontal direction between the reflection surface 72 and the reflection surface 73, so that in the present embodiment, the vibration amplitude at the monitoring object position can be obtained with higher precision than the conventional technology.

Also in the present embodiment, when monitoring the vibration state of the reactor internal in the RPV 1 using ultrasonic waves, the reflected echoes from the monitoring object can be identified easily.

Embodiment 6

Figure 15:
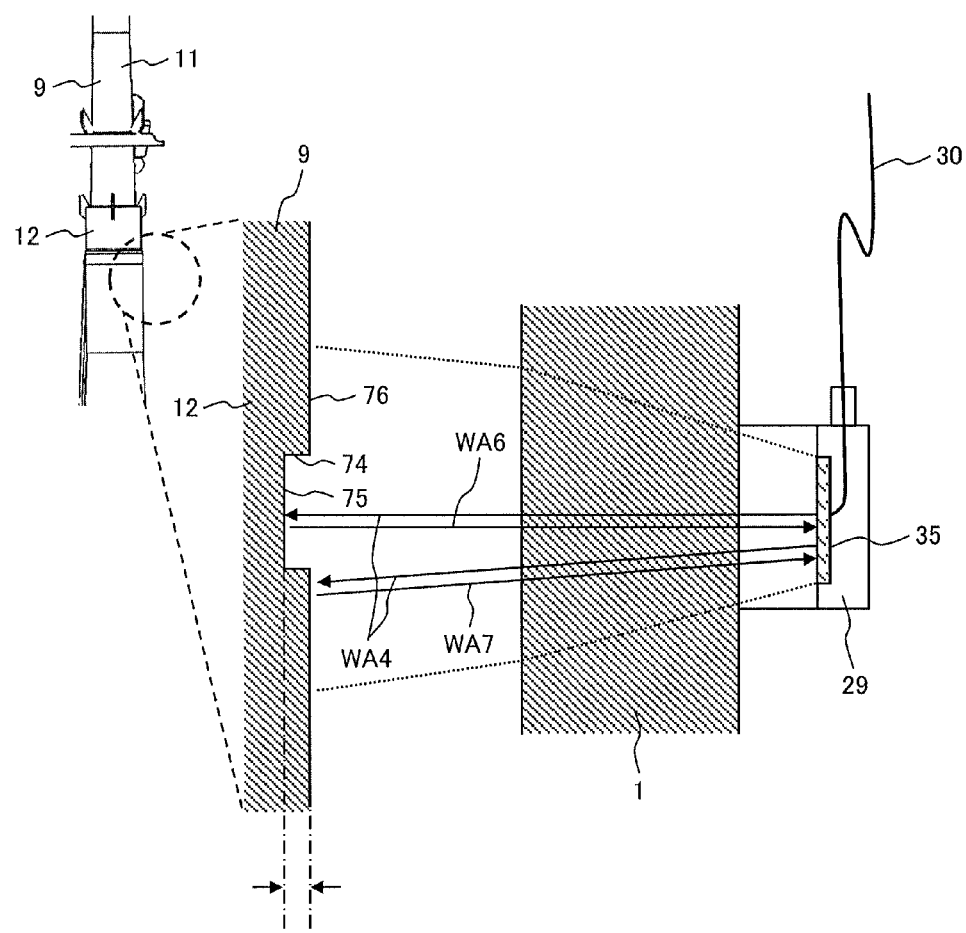
FIG. 15 is an explanatory drawing showing shape of a reflection plate used in a method of monitoring nuclear reactor vibration according to Embodiment 6 which is another preferable embodiment of the present invention.

A method of monitoring nuclear reactor vibration according to embodiment 6 which is another preferable embodiment of the present invention will be explained hereunder by referring to FIG. 15. The method of monitoring nuclear reactor vibration according to the present embodiment monitors the vibration of the jet pump being the reactor internal installed in the RPV 1 of the boiling water reactor.

In embodiments 2 to 5, the ultrasonic reflection plates having a plurality of reflection surfaces are attached at the morning object position on the outer surface of the jet pump 9. The present embodiment forms a plurality of hollows 74 on the outer surface of the vibration monitoring object, for example, the jet pump 9 facing the RPV 1 and uses the bottoms of the hollows 74 as reflection surfaces 75. The jet pump 9 is cylindrical, though the outer diameter of the diffuser 12 on a lower portion thereof is large such as about 200 mm, so that the hollows 74 can be formed easily on the outer surface of the diffuser 12. A thick flat portion is formed beforehand on the outside surface of the cast throat 11 to form the hollows 74 on the outer surface of the throat 11 with a small outer diameter on an upper part of the jet pump 9. The hollows 74 are processed on the flat portion, thus the reflection surfaces 75 can be formed. As a result, a reflection surface 76 which is the outer surface of the diffuser 12 and the reflection surfaces 75 are formed on the diffuser 12. Based on the time difference between the reflected wave WA6 and the reflected wave WA7 which are generated on the reflection surfaces 75 and 76 are received and the distance in the horizontal direction between the reflection surface 75 and the reflection surface 76, the sound speed of the reactor water at that time is obtained, so that in the present embodiment, the vibration amplitude at the monitoring object position can be obtained with higher precision than the conventional technology. Further, the reflection surfaces 75 are formed on the outer surface of the jet pump 9 by processing this outer surface, so that as in Embodiments 2 to 5, if some of the ultrasonic reflection plates attached to the outer surface of the jet pump 9 are dropped out by any chance, the vibration of the jet pump 9 can be prevented from impossible measurement.

Also in the present embodiment, when monitoring the vibration state of the reactor internal in the boiling water reactor using ultrasonic waves, the reflected echoes from the monitoring object can be identified easily. If the shapes shown in FIGS. 8 and 12 to 14 are processed, the shape of the ultrasonic reflection portion can have the similar functions.

REFERENCE SIGNS LIST

1: reactor pressure vessel, 4: core shroud, 5: core, 7: annular space (annulus portion), 9: jet pump, 10: nozzle, 11: throat, 12: diffuser, 17: slip joint, 18: gap, 23: bracket, 25: wedge, 29: ultrasonic sensor, 30: coaxial cable, 31, 31A: ultrasonic transmitter and receiver, 32, 32A: ultrasonic signal process section, 35: ultrasonic vibration element, 49, 49A, 49B, 49C: ultrasonic reflection plate, 52, 67, 68: hollow, 53, 54, 65, 66, 70-73, 75: reflection surface, 64: projection.

What is claimed is:

1. A nuclear reactor vibration monitoring apparatus comprising:
an ultrasonic sensor set on an outer surface of a reactor pressure vessel, the ultrasonic sensor transmitting ultrasonic waves and receiving reflected echoes thereof;
an ultrasonic transmitter and receiver for controlling simultaneous transmission of the ultrasonic waves to each of a plurality of reactor internals undergoing relative vibration in the reactor pressure vessel and reception of respective reflected echoes from respective reflection surfaces of respective reactor internals; and
an ultrasonic signal process apparatus for processing respective reflected echoes and calculating said relative vibration of the respective reflection surfaces of the respective reactor internals based on time differences between the respective reflected echoes reflected from the respective reflection surfaces.

2. The nuclear reactor vibration monitoring apparatus according to claim 1, wherein said ultrasonic signal process apparatus calculates the relative vibration by obtaining variations in distance between the reflection surfaces from detection time differences of the respective reflected echoes.

3. The nuclear reactor vibration monitoring apparatus according to claim 1, wherein the ultrasonic signal process apparatus calculates vibration displacements of the reflection surfaces.

4. The nuclear reactor vibration monitoring apparatus according to claim 1, wherein a range of recording time of the respective reflected echoes is decided based on waveforms of said respective reflected echoes.

5. The nuclear reactor vibration monitoring apparatus according to claim 1, wherein the ultrasonic sensor transmits the ultrasonic waves as one pulse or as a plurality of continuous pulses.

6. The nuclear reactor vibration monitoring apparatus according to claim 1, further comprising a reflection body installed on at least one of the reflection surfaces of said reactor internals.

7. The nuclear reactor vibration monitoring apparatus according to claim 1, wherein said reactor internals are a throat and a diffuser of a jet pump, a wedge and a bracket of the jet pump, or the throat and the bracket of the jet pump.

8. A method of monitoring nuclear reactor vibration comprising:

simultaneously transmitting ultrasonic waves to each of a plurality of reactor internals undergoing relative vibration in a reactor pressure vessel from an ultrasonic sensor set on an outer surface of a reactor pressure vessel;

receiving each reflected echo from respective reflection surfaces of respective reactor internals to which the ultrasonic waves are transmitted; and processing respective reflected echoes and calculating the relative vibration of the respective reflection surfaces of the respective reactor internals based on time differences between the respective reflected echoes reflected from the respective reflection surfaces.

9. The method of monitoring nuclear reactor vibration according to claim 8, wherein calculating the relative vibration is performed based on a detected time difference of the respective reflected waves.

10. The method of monitoring nuclear reactor vibration according to claim 8, further comprising calculating a vibration displacement of the reflection surfaces.

11. The method of monitoring nuclear reactor vibration according to claim 8, further comprising deciding a range of recording time of the respective reflected echoes based on waveforms of the respective reflected echoes.

12. The method of monitoring nuclear reactor vibration according to claim 8, wherein the ultrasonic waves are transmitted as one pulse or as a plurality of continuous pulses.

13. The method of monitoring nuclear reactor vibration according to claim 8, wherein the reactor internals are a throat and a diffuser of a jet pump, a wedge and a bracket of the jet pump, or the throat and the bracket of the jet pump.

14. The method of monitoring nuclear reactor vibration according to claim 10, comprising comparing an amplitude of the calculated relative vibration with a threshold value obtained by either a pre-analysis or evaluation at times of manufacture of the reactor internals, and determining either absence or presence of an abnormality.

* * * * *